United States Patent
Buczek

(10) Patent No.: US 6,705,474 B1
(45) Date of Patent: Mar. 16, 2004

(54) SURGICAL TOOL HOLDER

(75) Inventor: Mark J. Buczek, Oceanside, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/406,118

(22) Filed: Apr. 3, 2003

Related U.S. Application Data
(60) Provisional application No. 60/442,929, filed on Jan. 27, 2003.

(51) Int. Cl.[7] .................................................. A47F 7/00
(52) U.S. Cl. ...................................................... 211/70.6
(58) Field of Search ............................ 211/70.6, 126.6, 211/126.1, 85.13

(56) References Cited

U.S. PATENT DOCUMENTS

| | | | | |
|---|---|---|---|---|
| 3,774,773 A | * | 11/1973 | Brent | 211/70.6 |
| D249,362 S | * | 9/1978 | Forsman et al. | D24/230 |
| 5,170,804 A | * | 12/1992 | Glassman | 128/849 |
| 5,439,471 A | * | 8/1995 | Kerr | 606/174 |
| 5,624,454 A | * | 4/1997 | Palti et al. | 606/151 |
| 5,848,693 A | * | 12/1998 | Davis et al. | 206/370 |
| D447,567 S | * | 9/2001 | Murphy et al. | D24/172 |

* cited by examiner

*Primary Examiner*—Alvin Chin-Shue
*Assistant Examiner*—Sarah Purol
(74) *Attorney, Agent, or Firm*—Jeffrey S. Schira

(57) ABSTRACT

A surgical tool holder mounted on a surgical tray that is connected to the surgical console. The tool holder has a pair of opposing, spring-loaded gripper arms. The gripper arms will move apart under force, but rotate to a closed position when no force is applied. In the closed position, the opposing gripper arms and a small, curved-shaped gap between the gripper arms allows the tool holder to accommodate a wide variety diameters of handpieces or tools.

10 Claims, 3 Drawing Sheets

SURGICAL TOOL HOLDER

This application claims the benefit of U.S. Provisional Application Ser. No. 60/442,929, filed Jan. 27, 2003.

BACKGROUND OF THE INVENTION

This invention relates generally to the field of ophthalmic surgery and more particularly to surgical tray tool holders used with surgical consoles.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea, vitreous and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Alternatively, disease or trauma may affect the retina or vitreous, in many cases requiring that the vitreous be removed.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is usually replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

With respect to vitreous and/or retinal surgery, a variety of cutting devices, scissors, extrusion needles (cannulas), fragmenters or tissue manipulators may be used. Some of these devices, such as vitreous cutters, use a guillotine (axial) or reciprocating hollow cutting tube. Suction is applied to the interior of the cutting tube so that the tissue is aspirated away as it is cut.

The various irrigation and aspiration tubings connecting the various handpieces to the surgical console all must primed to remove any air in the system prior to surgery. Prior to the present invention, handpieces were primed by holding the handpiece tip in a small container of sterile irrigation fluid, or by placing an elastic priming chamber over the handpiece tip and initiating the pressurized flow of irrigating fluid. During this procedure, it is preferred that the open end of the tip be held pointed upward so that any air in the system will tend to exit the tip and enter the priming chamber. Although the priming sequence does not take a long time, priming still requires the attention of the operating room personnel.

Therefore, a need continues to exist for a hands-free priming devices of surgical instruments.

SUMMARY OF THE INVENTION

The present invention improves upon the prior art by providing a surgical tool holder mounted on a surgical tray that is connected to the surgical console. The tool holder has a pair of opposing, spring-loaded gripper arms. The gripper arms will move apart under force, but rotate to a closed position when no force is applied. In the closed position, the opposing gripper arms and a small, curved-shaped gap between the gripper arms allows the tool holder to accommodate a wide variety of diameters of handpieces or tools.

Accordingly, one objective of the present invention is to provide a surgical tray having a tool holder.

Another objective of the present invention is to provide a tool holder having a pair of opposing, spring-loaded gripper arms.

Another objective of the present invention is to provide a tool holder that allows for hand-free priming of surgical tools.

Another objective of the present invention is to provide a tool holder having a pair of opposing, spring-loaded gripper arms that accommodate a wide variety of handpiece sizes.

These and other advantages and objectives of the present invention will become apparent from the detailed description and claims that follow.

DETAILED DESCRIPTION OF THE INVENTION

Figure 1:
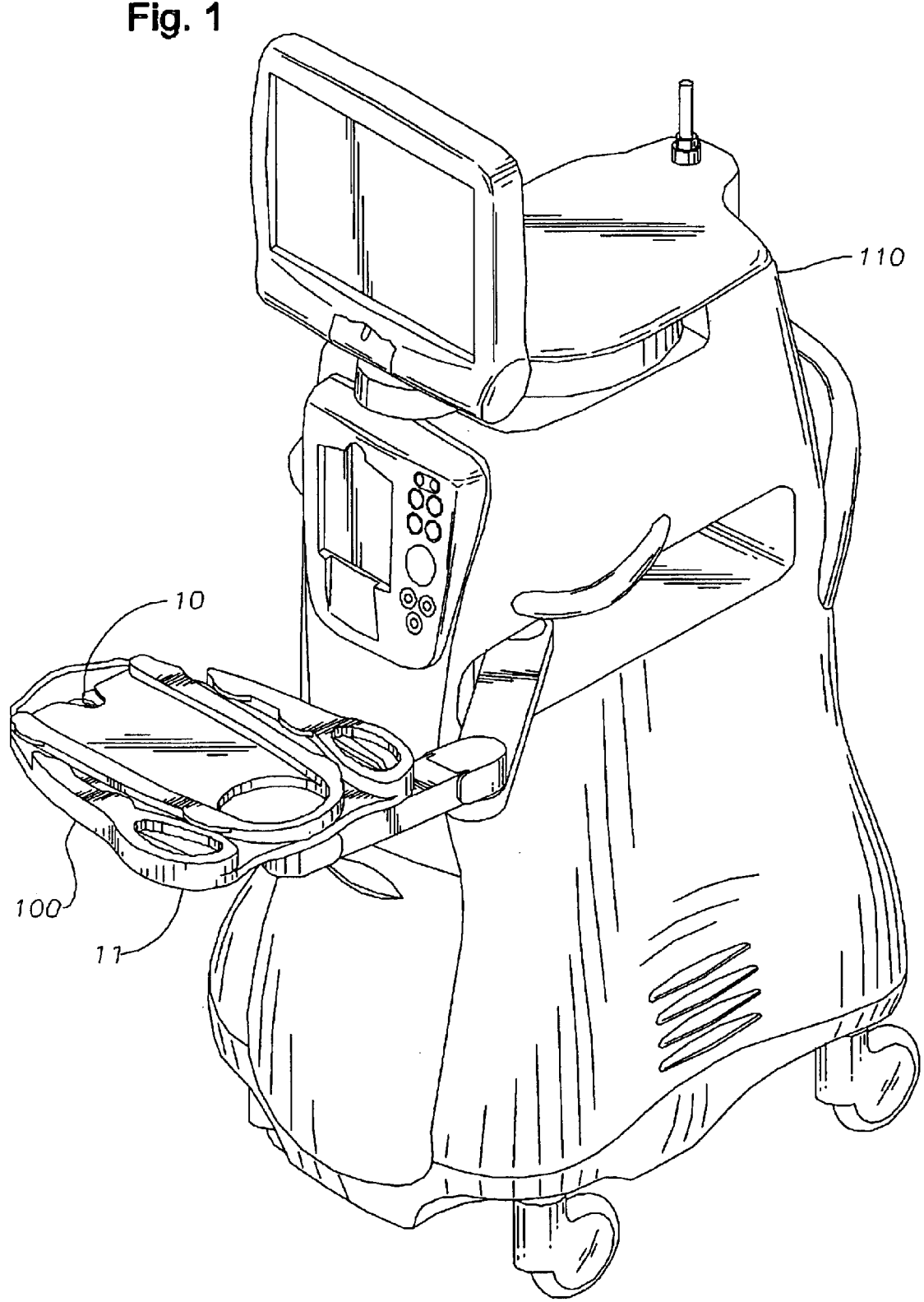
FIG. 1 is a perspective view of the tool holder of the present invention mounted on a surgical tray forming a part of a surgical console.
Figure 2:
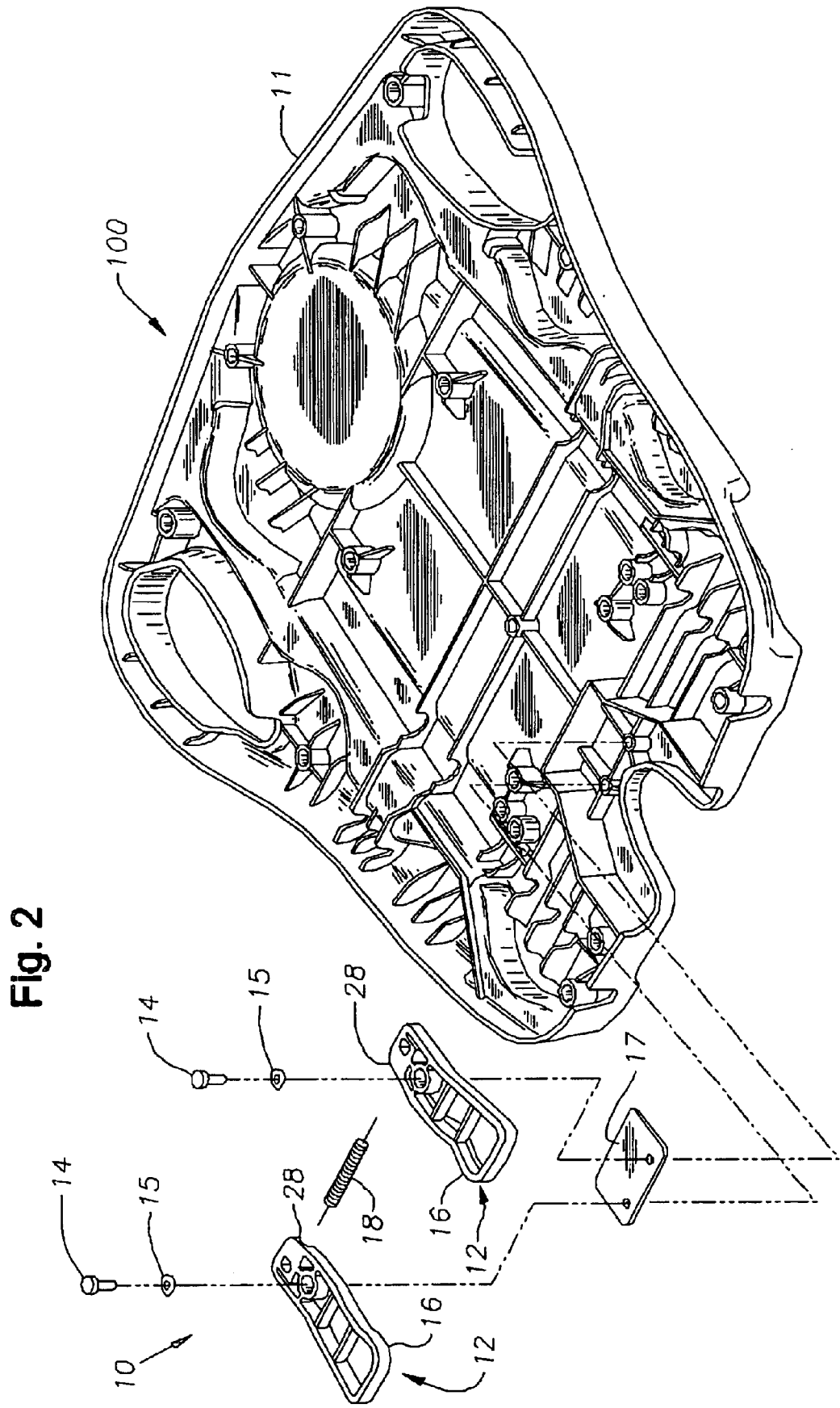
FIG. 2 is an exploded assembly view of the tool holder of the present invention mounted on a surgical tray.
Figure 3:
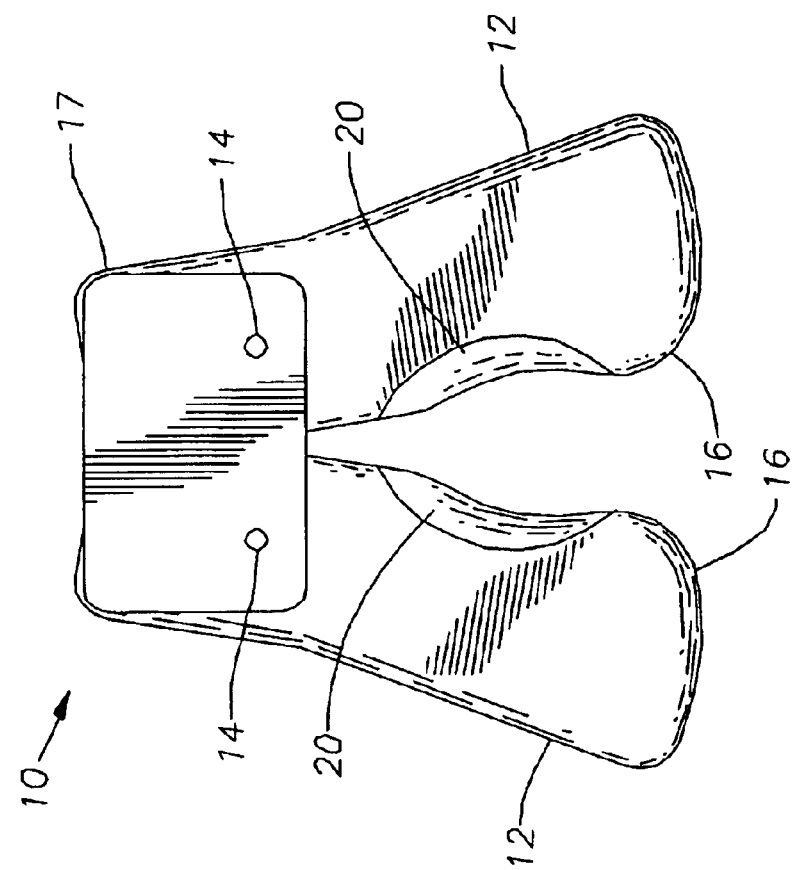
FIG. 3 is a top plan view of the tool holder of the present invention shown in the closed position.
Figure 4:
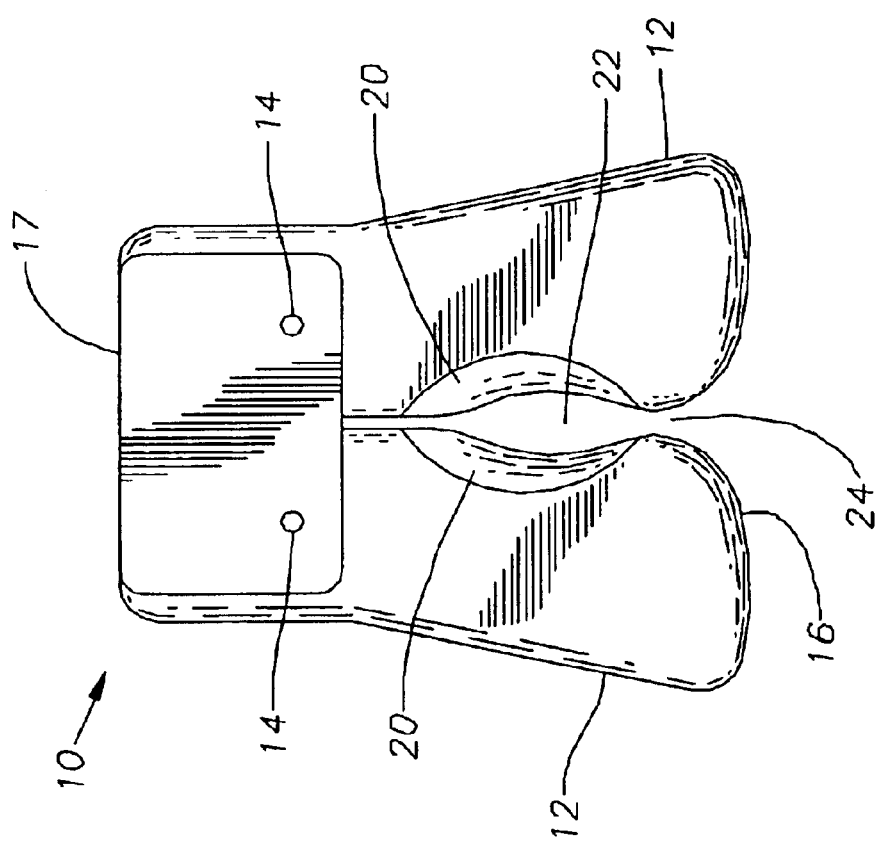
FIG. 4 is a top plan view of the tool holder of the present invention shown in the open position.

As best seen in FIG. 1, tool holder 10 of the present invention generally is connected to or forms a part of body 11 of surgical tray 100 attached to surgical console 110, such consoles being well-known in the art. For example, U.S. Pat. No. Des. 467,001, the entire contents of which being incorporated herein by reference, discloses a surgical console suitable for use with tool holder 10 of the present invention. As best seen in FIGS. 2 and 3, tool holder 10 generally contains gripper arms 12 mounted to tray 100 by pivot pins 14 and spring washers 15. Opening jaws 16 of arms 12 are opposite spring 18 and are slightly rounded and are biased toward each other by compression spring 18. Heal portions 28 of arms 12 are formed at a slight angle to allow limited rotation of arms 12 via interaction between heal portions 28. Arms 12 contain arcuate surfaces 20 that form gap 22 when jaws 16 are pushed together by spring 18. Gap 22 allows for tool holder 10 to hold tools of a variety of diameters, sizes and weights. The rounded nature of jaws 16, along with spacing 24 between jaws 16, provides for easier insertion of the tool (not shown) into tool holder 10. Arms 12 preferably are overmolded or combined with a suitably grippy material, such as thermal plastic elastomer (TPE) in the arcuate region. Plate 17 provides a smooth bearing surface for arms 12 as arms 12 are pressed against plate 17 by spring washers 15.

In use, the surgical tool is pushed against rounded jaws 16 and into space 24. Arms 12 pivot about pins 14, compressing spring 18, until the tool is located within gap 22. Once the tool is located within gap 22, arcuate surfaces 20 are forced against the tool by spring 18, thereby holding the tool within tool holder 10.

This description is given for purposes of illustration and explanation. It will be apparent to those skilled in the relevant art that changes and modifications may be made to the invention described above without departing from its scope or spirit.

I claim:

1. A tool holder, comprising:
   a) a pair of opposing, pivoting arms, the arms having jaws and arcuate surfaces, the arcuate surfaces defining a gap when the arcuate surfaces are biased together; and
   b) a spring connecting the arms located opposite the jaws and acting to bias the jaws together.

2. The tool holder of claim 1 further comprising a grippy surface on the arcuate surfaces.

3. The tool holder of claim 2 wherein the grippy surface is a thermal plastic elastomer.

4. The tool holder of claim 3 wherein the thermal plastic elastomer is overmolded onto the arcuate surfaces.

5. An surgical tray, comprising:
   a) a body;
   b) a pair of opposing, pivoting arms, the arms having jaws and being connected to the body; and
   c) a spring connecting the arms located opposite the jaws and acting to bias the jaws together.

6. The surgical tray of claim 5 further comprising a grippy surface on the arms.

7. The surgical tray of claim 6 wherein the grippy surface is a thermal plastic elastomer.

8. The surgical tray of claim 7 wherein the thermal plastic elastomer is overmolded onto the arms.

9. A tool holder, comprising:
   a) a pair of opposing, pivoting arms, the arms having jaws and arcuate surfaces, the arcuate surfaces being overmolded with a thermal plastic elastomer; and
   b) a spring connecting the arms located opposite the jaws and acting to bias the jaws together.

10. A surgical tray, comprising:
    a) a body;
    b) a pair of opposing, pivoting arms, the arms having jaws overmolded with a thermal plastic elastomer and being connected to the body; and
    c) a spring connecting the arms located opposite the jaws and acting to bias the jaws together.

\* \* \* \* \*